United States Patent [19]

Lucadamo et al.

[11] Patent Number: 4,720,294

[45] Date of Patent: Jan. 19, 1988

[54] DEPHLEGMATOR PROCESS FOR CARBON DIOXIDE-HYDROCARBON DISTILLATION

[75] Inventors: Gene A. Lucadamo, Macungie; Howard C. Rowles, Center Valley, both of Pa.

[73] Assignee: Air Products and Chemicals, Inc., Allentown, Pa.

[21] Appl. No.: 893,506

[22] Filed: Aug. 5, 1986

[51] Int. Cl.[4] .................... F25J 3/02

[52] U.S. Cl. .................... 62/31; 62/28

[58] Field of Search .................... 62/11, 17, 20, 22, 23, 62/24, 27, 28, 30, 31, 32, 41

[56] References Cited

U.S. PATENT DOCUMENTS

| | | | |
|---|---|---|---|
| 3,392,536 | 7/1968 | Smith | 62/30 X |
| 4,002,042 | 1/1977 | Pryor et al. | 62/28 |
| 4,158,467 | 6/1979 | Larson et al. | 299/2 |
| 4,270,937 | 6/1981 | Adler et al. | 62/17 |
| 4,270,939 | 6/1981 | Rowles et al. | 62/22 |
| 4,293,322 | 10/1981 | Ryan et al. | 62/17 |
| 4,318,723 | 3/1982 | Holmes et al. | 62/20 |
| 4,350,511 | 9/1982 | Holmes et al. | 62/17 |
| 4,383,841 | 5/1983 | Ryan et al. | 62/17 |
| 4,383,842 | 5/1983 | O'Brien | 62/20 |
| 4,417,449 | 11/1983 | Hegarty et al. | 62/28 |
| 4,428,759 | 1/1984 | Ryan et al. | 62/28 X |
| 4,451,275 | 5/1984 | Vines et al. | 62/28 |
| 4,453,956 | 6/1984 | Fabbri et al. | 62/18 |
| 4,519,824 | 5/1985 | Huebel | 62/26 |
| 4,519,825 | 5/1985 | Bernhard et al. | 62/28 |
| 4,561,869 | 12/1985 | Gazzi et al. | 62/17 |
| 4,602,477 | 7/1986 | Lucadamo | 62/31 X |

OTHER PUBLICATIONS

"Membranes for Natural Gas Sweetening and $CO_2$ Enrichment," Chemical Engineering Progress, Oct. 1982, pp. 38–43.

*Primary Examiner*—Henry C. Yuen

*Assistant Examiner*—Steven E. Warner

*Attorney, Agent, or Firm*—Willard Jones, II; James C. Simmons; William F. Marsh

[57] ABSTRACT

A low capital cost, energy efficient process for separation of carbon dioxide, sulfide gases and hydrocarbons from carbonaceous off-gas streams, for example, oil shale retorting off-gases, coal gasification off-gases, oxygen fire flooding off-gases or carbon dioxide miscible flood enhanced oil recovery off-gases is disclosed. The process comprises separation of the off-gases into an essentially sulfur-free light fuel gas, a heavy hydrocarbon stream and a carbon dioxide gas stream wherein the off-gas is compressed if necessary and cooled prior to separation of the various streams in a distillation column. The carbon dioxide stream is expanded in an auto-refrigeration step to provide some of the necessary process refrigeration.

8 Claims, 2 Drawing Figures

DEPHLEGMATOR PROCESS FOR CARBON DIOXIDE-HYDROCARBON DISTILLATION

TECHNICAL FIELD OF THE INVENTION

The present invention relates to a process to separate and remove carbon dioxide, sulfide gases and hydrocarbons from carbonaceous off-gases.

BACKGROUND OF THE INVENTION

Several processes have been used commercially or have been proposed to separate carbon dioxide, sulfide gases and hydrocarbons from carbonaceous off-gases.

The Ryan/Holmes process which is disclosed in U.S. Pat. Nos. 4,293,322; 4,318,723; 4,350,511 and 4,383,841 is an extractive distillation process specifically for high carbon dioxide gas processing which utilizes a natural gas liquid column additive to separate the carbon dioxide from methane, carbon dioxide from ethane, and carbon dioxide from hydrogen sulfide. Incremental energy costs for higher propane recovery, e.g. above 30%, exceed recovered $C_3$ incremental revenues.

Carbon dioxide is separated from light hydrocarbons by permeation through a suitable membrane in a process described in "Membranes for Natural Gas Sweetening and $CO_2$ Enrichment", Chemical Engineering Progress, October 1982, Pages 38–43. Carbon dioxide permeate is produced at low pressure and recompression is very energy intensive. Both the $CO_2$ recompressor and the membranes are high in capital cost.

Various absorbent solvents have also been utilized to absorb $CO_2$ from carbonaceous off-gases. In these processes, the carbon dioxide is recovered from the solvent at low pressure, such processes being generally energy intensive in both thermal and compression energy and requiring high capital expenditures. Typical solvent absorbent processes are described in U.S. Pat. Nos. 4,158,467 and 4,270,937.

U.S. Pat. No. 4,417,449 discloses a process in which carbonaceous off-gases are separated in a distillation column into an overhead fuel gas stream, a carbon dioxide-sulfide liquid sidestream and a heavy hydrocarbon-carbon dioxide liquid bottom fraction. The bottom fraction is further separated into a recycled carbon dioxide stream and a product natural gas liquid stream. The process requires relatively low energy and capital.

BRIEF SUMMARY OF THE INVENTION

The present invention relates to a process for the separation of a carbonaceous off-gas stream containing a quantity of acid gases, such as carbon dioxide, hydrogen sulfide and carbonyl sulfide, by separating the off-gas stream into an essentially sulfur-free, light fuel gas, an acid gas stream and a heavy hydrocarbon stream, wherein the separation is accomplished in a low temperature distillation column, preferably a two section or two-tier distillation column. The present invention further incorporates a dephlegmator with the distillation column to provide reflux for the column, thereby eliminating the need for external condensers. Refrigeration for the dephlegmator is provided predominantly by heat exchanging a portion of a liquefied acid gas stream and a subcooled column bottoms stream. The liquefied acid gas stream is split into two substreams; the first substream is recycled to the lower section of the column as reflux. The second substream is subcooled, if necessary, then flashed and heat exchanged to provide refrigeration for the dephlegmator. At least a portion of the column bottoms are subcooled in heat exchange with warming process streams and then flashed and heat exchanged to provide refrigeration for the dephlegmator.

DETAILED DESCRIPTION OF THE INVENTION

The present invention is a process to separate carbonaceous gases, typically produced by shale oil retorting, coal gasification, oxygen-fire flooding, or carbon dioxide miscible flood enhanced oil recovery, by low temperature distillation. Generally, a carbonaceous gas can be described as one comprising acid gases, e.g. carbon dioxide, hydrogen sulfide, or carbonyl sulfide, and hydrocarbon gases. It may also contain non-hydrocarbon gases, such as carbon monoxide, hydrogen, nitrogen or oxygen. In the process of the present invention, the carbonaceous gas is separated into a light hydrocarbon gas stream, e.g. methane, an acid gas stream, e.g, carbon dioxide, and a heavy hydrocarbon stream, e.g. $C_3^+$. To better describe the present invention, the process will be described in an embodiment to separate a carbonaceous gas produced by carbon dioxide miscible flood enhanced oil recovery.

Figure 1:
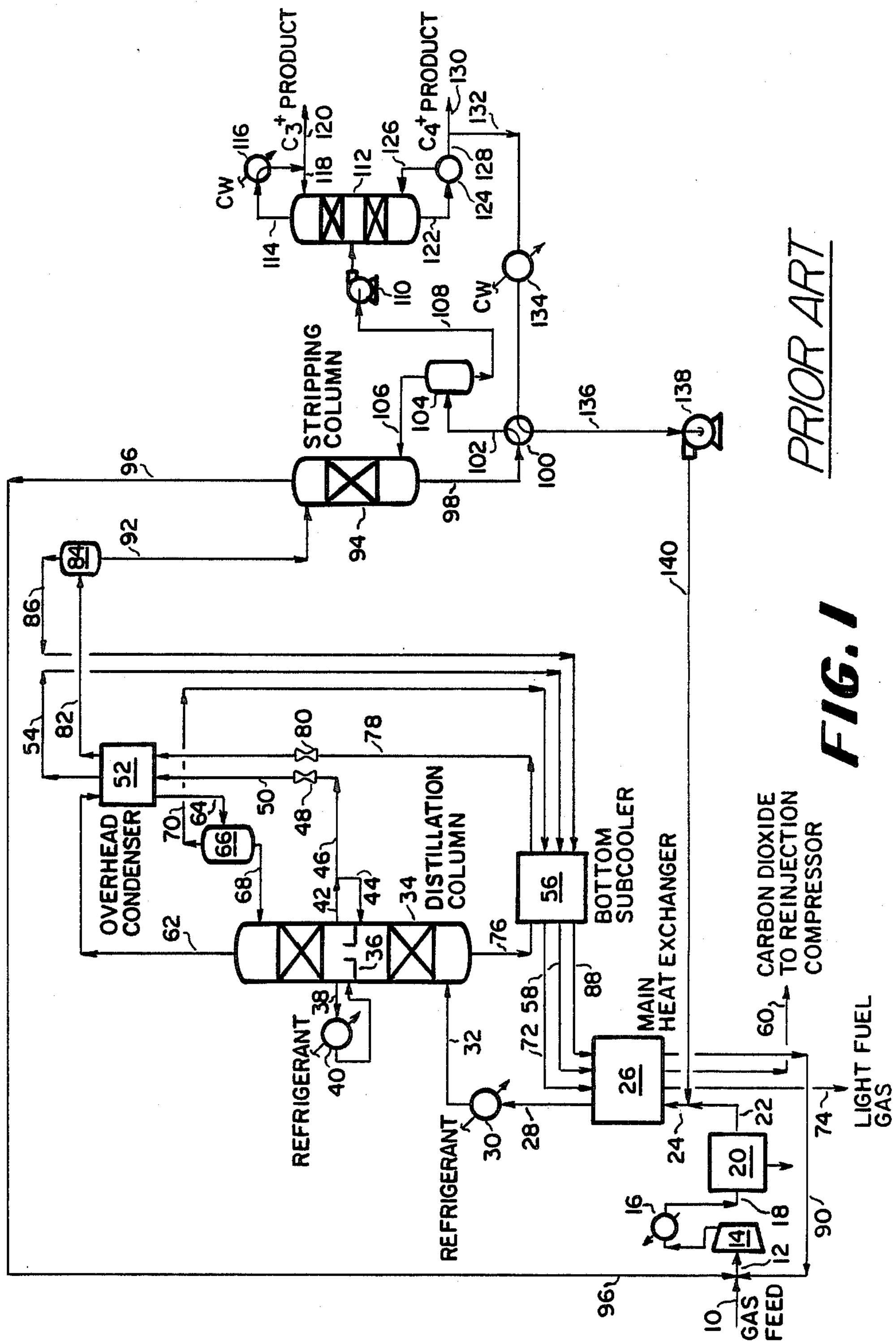
FIG. 1 is a schematic diagram detailing a distillation process as disclosed in the prior art.

A process to separate carbon dioxide, light hydrocarbons and natural gas liquids from a carbon dioxide enhanced oil recovery associated off-gas is shown in FIG. 1. This process is based on U.S. Pat. No. 4,417,449 and achieves 95% recovery of 95% purity carbon dioxide for reinjection into the well head, 90% recovery of methane as light fuel gas, 70% recovery of propane and essentially 100% recovery of $C_4^+$ hydrocarbons as a natural gas liquids product. As shown in FIG. 1, the gas feed stream, via line 10, at 65 psi, 100° F. is mixed with carbon dioxide recycle gas streams from the process, via lines 90 and 96, into a combined feed stream, line 12, and is processed in a compression and aftercooling process stage wherein the combined feed stream is compressed to 385 psia in compressor 14 and aftercooled in heat exchanger 16 before passing into dehydrator 20, via line 18. The required dehydration can be performed by any conventional methods, i.e. molecular sieve adsorption, glycol wash or methanol injection.

A liquid $C_4^+$ recycle stream 140 is added to dehydrated feed gas stream 22 to facilitate higher propane recovery. This two-phase mixture, in line 24, enters main heat exchanger 26 where it is cooled and partially condensed against warming process streams and leaves main heat exchangerr 26 via line 28. Supplemental feed refrigeration is provided downstream of main heat exchanger 26 in refrigeration heat exchanger 30 to cool the feed to approximately 60° F.

The cooled feed stream, now in line 32, is then introduced into the bottom of a two-section low temperature distillation column 34 at 381 psia. Column 34 is patitioned by a liquid trap-out plate 36 at the midsection of column 34, plate 36 allowing for withdrawal of the upper column reflux. A side stream, via line 38, is withdrawn from column 34 and fed to side condenser 40 to generate additional carbon dioxide reflux for the lower section of column 34. Condensed side stream 38 is returned to column 34 at the top of plate 36.

In the lower portion of column 34, the carbon dioxide reflux, which enters the lower portion of column 34 via line 44, is contacted with the feed gas to produce a liquid bottoms fraction comprised largely of $C_3$+ hydrocarbons and carbon dioxide. This bottom fraction is removed from column 34, via line 76, and is further processed for recovery of the natural gas liquids product and a $C_4$+ natural gas liquids recycle stream. The uncondensed portion of the feed gas rises through column 34 and passes through trap-out plate 36 into the upper section at 380 psia and 8° F. By additional contacting with carbon dioxide reflux, the upper section of the distillation column separates this portion of the feed into a $C_1$, $C_2$ and carbon dioxide overhead, which is removed via line 62, at −13° F. and a $CO_2$ liquid stream, which is removed from column 34 via line 42.

The $CO_2$ liquid stream, in line 42, which was condensed in either the overhead condenser 52 or side condenser 40 is removed from column 34 at trap-out plate 36. Part of this $CO_2$ liquid stream in line 42 at 380 psia, 7° F., is returned, via line 44, to the lower section of column 34 to provide reflux. The remainder in line 46 is cooled by Joule-Thompson expansion to 105 psia through J-T valve 48. This cooled two-phase portion, in line 50, at −58° F. is vaporized for refrigeration in overhead condenser 52. The vaporized $CO_2$ stream in line 54 is then warmed in bottom subcooler 56, and finally warmed in main heat exchanger 26. The warm $CO_2$ gas stream in line 60 at 100 psia, 90° F., could then be compressed to reinjection pressure, e.g., 2000 psia, and recycled to the enhanced oil recovery project. This compression and recycle step is not shown in the figure.

The overhead stream 62 from distillation column 34 is cooled to −51° F. in overhead condenser 52 and introduced into fuel gas separator 66, via line 64. A carbon dioxide-rich reflux stream, typically about 60% carbon dioxide, is condensed from column 34 overhead stream 62 and returned, via line 68, as reflux to the upper section of distillation column 34. An overhead stream is removed from fuel gas separator 66, via line 70; this overhead is the light fuel gas product, which is rich in methane and ethane, and typically contains about 25% to 35% carbon dioxide. Refrigeration is recovered from stream 70 by warming the stream in bottom subcooler 56 and main heat exchanger 26; the light fuel gas is removed from the process, via line 74, and is delivered at 370 psia, 90° F.

Since refrigeration in overhead condenser 52 is supplied in part by vaporization of the expanded $CO_2$-rich stream in line 50, the minimum temperature for fuel gas separator 66 is about −55° F.; this is required in order to avoid formation of solid $CO_2$ in the condenser. The operating pressure for distillation column 34 is selected so that the loss of carbon dioxide in the light fuel gas, in line 70, from fuel gas separator 66 is maintained at a tolerable level. The higher the operating pressure, the lower the carbon dioxide loss. Typically operating pressures for column 34 are in the range of 200 to 650 psia, and preferably in the range of 250 to 500 psia.

The hydrocarbon-carbon dioxide liquid stream removed, via line 76 from the bottom of distillation column 34 at 37° F. is subcooled to 0° F. in bottom subcooler 56. This subcooled stream in line 78 is then expanded to 70 psia through J-T valve 80 to provide additional refrigeration for overhead condenser 52. This two-phase stream at −20° F. then proceeds via line 82 from condenser 52 to carbon dioxide recycle separator 84. Bottom subcooler 56 and main heat exchanger 26 recover refrigeration from the carbon dioxide-rich separator overhead vapor stream, in line 86; this warmed stream is then recycled, via line 90, to feed gas compressor 14 at 65 psia. The recycle rate is set to provide the required carbon dioxide for adequate reflux in the column to achieve the desired propane recovery, for example 70% in the material balance provided in Table 1.

The liquid bottoms stream from carbon dioxide recycle separator 84, which is predominately $C_3$+ hydrocarbons, is introduced via line 92 into stripping column 94. This column 94 strips the residual $CO_2$ and some of the hydrogen sulfide, if present, from the heavy hydrocarbon liquid. The overhead vapor stream from stripping column 94, which is predominately carbon dioxide, is recycled back via line 96 to feed gas compressor 14 at 65 psia where it is mixed with feed gas stream 10 along with the overhead vapor from $CO_2$ recycle separator 84, via line 90.

A bottoms liquid stream is removed from stripping column 94, via line 98. This bottoms stream is partially vaporized in heat exchanger 100 and fed, via line 102, to separator 104. The vapor phase from separator 104 is returned, via line 106, to the bottom of stripping column 94. The liquid phase from separator 104 is pumped by pump 110 via line 108 to a final natural gas liquids distillation column 112 which separates it into an overhead $C_3$+ natural gas liquids product stream, in line 120, and a bottom $C_4$+ stream, in line 128. Essentially all of the $H_2S$, ethane and propane in the feed to the column will be recovered as overhead product. The column overhead vapor stream, in line 114, is condensed in heat exchanger 116; a portion of the condensed overhead is returned to column 112 as reflux, via line 118; the remainder is removed as product via line 120. The bottoms stream, in line 122, is reboiled in reboiler 124; the vapor from reboiler 124 is returned to the bottom of column 112, via line 126. The liquid phase from reboiler 124 is split into a $C_4$+ natural gas liquids product stream, which is removed via line 130, and a $C_4$+ natural gas liquids recycle stream, which is returned to the process feed in line 132. This recycle stream, in line 132, is partially cooled with cooling water in heat exchanger 134, is used to provide stripping column 94 reboiler duty in heat exchanger 100, and is recombined with the feed stream, in line 22, pumped by recycle pump 138 via line 140.

An overall material balance for the aforedescribed process as depicted in FIG. 1 is provided in Table 1.

TABLE I

PRODUCT YIELDS, COMPOSITIONS, & RECOVERIES* FIG. 1 PROCESS

| | FEED | CARBON DIOXIDE | | | FUEL GAS | | | $C_3^+$ & $C_4^+$ PRODUCTS | | |
|---|---|---|---|---|---|---|---|---|---|---|
| Stream NUMBER | 10 | 60 | | | 74 | | | 120 & 130 | | |
| | MOLE % | # MOL/HR | MOLE % | % RECOVERED | # MOL/HR | MOLE % | % RECOVERED | # MOL/HR | MOLE % | % RECOVERED |
| TEMPERATURE: °F. | 100 | | 90 | | | 90 | | | 130 | |
| PRESSURE: PSIA | 65 | | 100 | | | 370 | | | 200 | |
| COMPONENT | | | | | | | | | | |
| $N_2$ | 0.33 | 0.02 | 0.02 | | 0.31 | 2.36 | | — | — | |
| $H_2S$ | 0.91 | 0.67 | 0.81 | 73.6 | — | — | | 0.24 | 5.36 | |
| $CO_2$ | 82.36 | 78.52 | 95.32 | 95.3 | 3.83 | 29.15 | | 0.01 | 0.22 | |
| $CH_4$ | 7.88 | 0.79 | 0.96 | | 7.09 | 53.95 | 90.0 | — | — | |
| $C_2H_6$ | 3.80 | 1.54 | 1.87 | | 1.91 | 14.54 | 50.3 | 0.35 | 7.81 | |
| $C_3H_8$ | 2.78 | 0.83 | 1.01 | | — | — | | 1.95 | 43.53 | 70.1 |
| $C_4H_{10}$ | 1.32 | 0.01 | 0.01 | | — | — | | 1.31 | 29.24 | 99.2 |
| $C_5H_{12}$ | 0.42 | — | — | | — | — | | 0.42 | 9.38 | 100.0 |
| $C_6^+$ | 0.20 | — | — | | — | — | | 0.20 | 4.46 | 100.0 |
| TOTAL | 100.00 | 82.38 | 100.00 | | 13.14 | 100.00 | | 4.48 | 100.00 | |

*Based on 100 MOL/HR of feed and 385 PSIA operating pressure.

Figure 2:
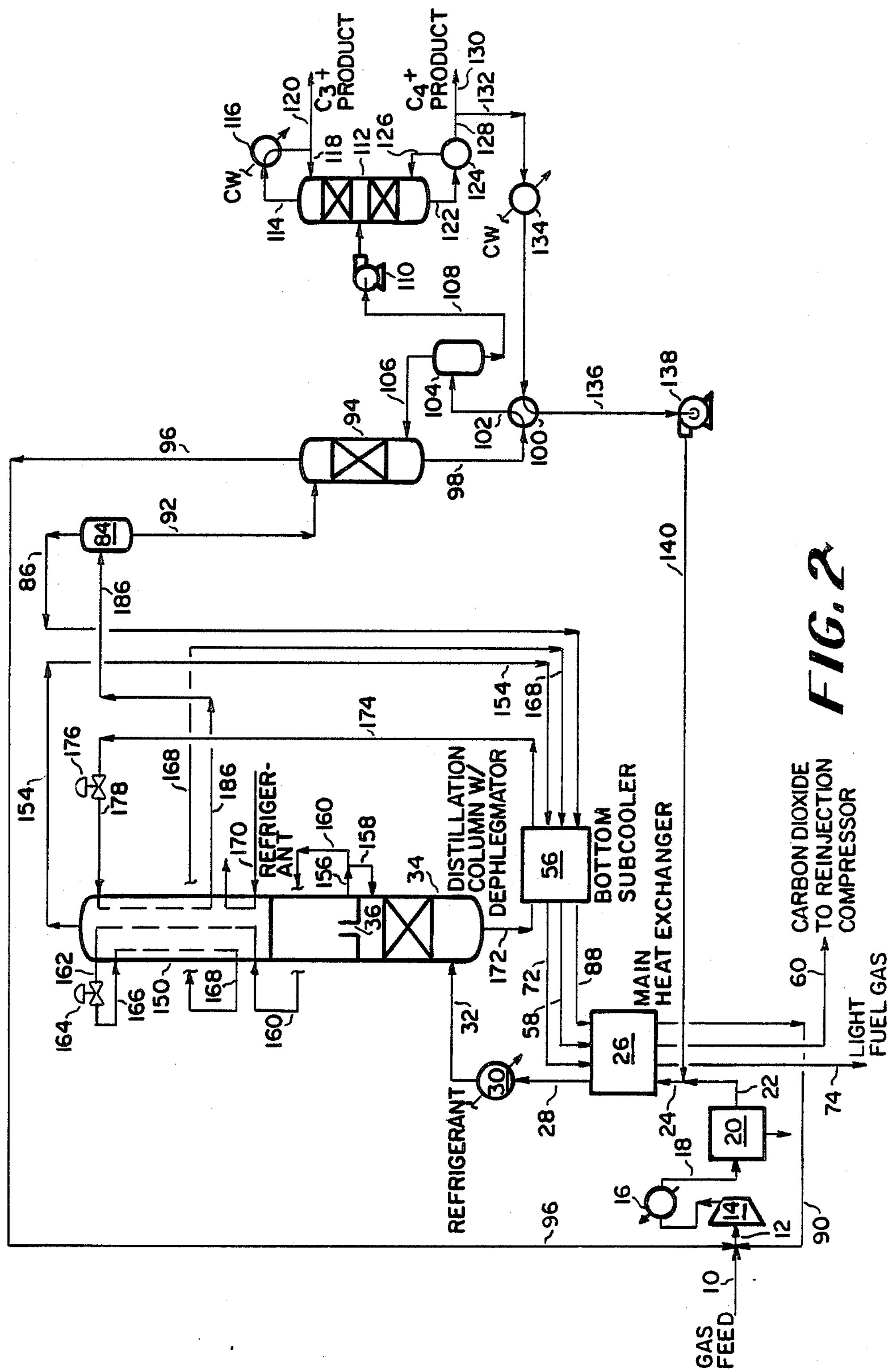
FIG. 2 is a schematic diagram of the process of the present invention.

FIG. 2 illustrates the process of the present invention which is an improvement of the process depicted in FIG. 1. The process of FIG. 2 includes a dephlegmator as the top section of low temperature distillation column 34 thereby incorporating side condenser 40 and overhead condenser 52 of FIG. 1 into the dephlegmator. Due to this incorporation, fuel gas separator 66 is eliminated.

Except for the dephlegmator section of distillation column 34, the operating conditions are essentially the same as the process depicted in FIG. 1. The uncondensed portion of the feed from the bottom section of distillation column 34 enters dephlegmator 150 at 380 psia and 8° F. This vapor stream is cooled to −55° F. in dephlegmator 150 to produce an overhead light fuel gas stream, which is removed from dephlegmator 150 in line 154, and a liquid $CO_2$ stream which is removed in line 156 via trap-out plate 36. Part of this stream, in line 156, at 380 psi and 7° F., is returned via line 158 to the lower portion of column 34 to provide reflux. The remainder, via line 160, is subcooled to −55° F. in dephlegmator 150, flashed to 255 psia through J-T valve 164 and revaporized in dephlegmator 150. This vaporized $CO_2$ is then removed from dephlegmator 150 and is fed to, via line 168, and warmed in bottom subcooler 56 and main heat exchanger 26. The warm carbon dioxide stream, in line 60, at 250 psia and 90° F. would then be compressed to reinjection pressure and recycled to the enhanced oil recovery project. This compression and recycle step is not shown. The more efficient refrigeration usage of the dephlegmator permits the carbon dioxide product stream 60 to be recovered at 250 psia rather than 100 psia as in the process depicted in FIG. 1.

The hydrocarbon-carbon dioxide liquid stream 172 removed from the bottom of the distillation column 34 at 37° F. is subcooled to 0° F. and expanded to 70 psia through J-T valve 176 as in the original process. This is done to provide additional refrigeration in dephlegmator 150. If necessary, auxiliary refrigeration can be introduced into the dephlegmator through line 170. Downstream carbon dioxide separation, stripping and natural gas liquids distillation are essentially identical to that of the original process. The amount of auxiliary refrigeration required in the feed chiller 30 and in the bottom of the dephlegmator, via line 170, is also essentially the same as in the original process. As indicated in the overall material balance of Table 2, the recovery of carbon dioxide gas for reinjection and the recovery of methane in the light fuel gas stream are somewhat higher with the improved process and the natural gas liquid products are unchanged. The major difference between the process of FIG. 1 and the improved process of FIG. 2 is in the significantly higher recovery pressure of the carbon dioxide reinjection product, stream 60, which in turn provides a substantial power savings advantage. Table 3 provides a material balance for the improved process at various points throughout the process.

TABLE II

PRODUCT YIELDS, COMPOSITIONS, & RECOVERIES* FIG. 2 PROCESS

| | FEED | CARBON DIOXIDE | | | FUEL GAS | | | $C_3^+$ & $C_4^+$ PRODUCTS | | |
|---|---|---|---|---|---|---|---|---|---|---|
| Stream NUMBER | 10 | 60 | | | 74 | | | 120 & 130 | | |
| | MOLE % | # MOL/HR | MOLE % | % RECOVERED | # MOL/HR | MOLE % | % RECOVERED | # MOL/HR | MOLE % | % RECOVERED |
| TEMPERATURE: °F. | 100 | | 90 | | | 90 | | | 130 | |
| PRESSURE: PSIA | 65 | | 250 | | | 370 | | | 200 | |
| COMPONENT | | | | | | | | | | |
| $N_2$ | 0.33 | 0.02 | 0.02 | | 0.31 | 2.47 | | — | — | |
| $H_2S$ | 0.91 | 0.67 | 0.81 | 73.6 | — | — | | 0.24 | 5.36 | |
| $CO_2$ | 82.36 | 78.92 | 95.13 | 95.8 | 3.43 | 27.35 | | 0.01 | 0.22 | |
| $CH_4$ | 7.88 | 0.75 | 0.90 | | 7.13 | 56.86 | 90.5 | — | — | |

TABLE II-continued

PRODUCT YIELDS, COMPOSITIONS, & RECOVERIES* FIG. 2 PROCESS

| | STREAM NAME | | | | | | | | | |
|---|---|---|---|---|---|---|---|---|---|---|
| | FEED | CARBON DIOXIDE | | | FUEL GAS Stream NUMBER | | | $C_3^+$ & $C_4^+$ PRODUCTS | | |
| | 10 | 60 | | | 74 | | | 120 & 130 | | |
| | MOLE % | # MOL/HR | MOLE % | % RECOVERED | # MOL/HR | MOLE % | % RECOVERED | # MOL/HR | MOLE % | % RECOVERED |
| $C_2H_6$ | 3.80 | 1.77 | 2.13 | | 1.67 | 13.32 | 44.0 | 0.35 | 7.81 | |
| $C_3H_8$ | 2.78 | 0.83 | 1.00 | | — | — | | 1.95 | 43.53 | 70.1 |
| $C_4H_{10}$ | 1.32 | 0.01 | 0.01 | | — | — | | 1.31 | 29.24 | 99.2 |
| $C_5H_{12}$ | 0.42 | — | — | | — | — | | 0.42 | 9.38 | 100.0 |
| $C_6^+$ | 0.20 | — | — | | — | — | | 0.20 | 4.46 | 100.0 |
| TOTAL | 100.00 | 82.97 | 100.00 | | 12.54 | 100.00 | | 4.48 | 100.00 | |

*Based on 100 MOL/HR of feed and 385 PSIA operating pressure.

TABLE III

MATERIAL BALANCE FIG. 2 PROCESS

| | STREAM NUMBER | | | | | | | | | | | | | | | |
|---|---|---|---|---|---|---|---|---|---|---|---|---|---|---|---|---|
| | 10 | 90 | 96 | 12 | 140 | 24 | 32 | 154 | 74 | 160 | 60 | 172 | 186 | 120 | 130 | 132 |
| PHASE* | V | V | V | V | L | V & L | V & L | V | V | L | V | L | V & L | L | L | L |
| TEMPERATURE: °F. | 100 | 90 | −19 | 92 | 100 | 101 | 60 | −55 | 90 | 7 | 90 | 37 | −20 | 99 | 305 | 305 |
| PRESSURE: PSIA | 65 | 65 | 70 | 65 | 382 | 382 | 380 | 380 | 375 | 380 | 250 | 381 | 70 | 200 | 200 | 200 |
| TOTAL FLOW: # MOL/HR | 100.0 | 31.6 | 7.0 | 138.6 | 30.0 | 168.6 | 168.6 | 12.5 | 12.5 | 83.0 | 83.0 | 73.1 | 73.1 | 3.9 | 0.6 | 30.0 |
| COMPONENT FLOW: # MOL/HR | | | | | | | | | | | | | | | | |
| $CO_2$ | 82.4 | 27.9 | 6.2 | 116.5 | — | 116.5 | 116.5 | 3.4 | 3.4 | 78.9 | 78.9 | 34.1 | 34.1 | — | — | — |
| $C_1$–$C_2$ | 11.7 | 2.2 | 0.45 | 14.3 | — | 14.3 | 14.3 | 8.8 | 8.8 | 2.55 | 2.55 | 3.0 | 3.0 | 0.35 | — | — |
| $C_3$ | 2.8 | 0.7 | 0.15 | 3.6 | — | 3.6 | 3.6 | — | — | 0.8 | 0.8 | 2.8 | 2.8 | 1.95 | — | — |
| $C_4^+$ | 1.9 | 0.4 | 0.1 | 2.4 | 30.0 | 32.4 | 32.4 | — | — | — | — | 32.4 | 32.4 | 1.35 | 0.6 | 30.0 |

*V = VAPOR
L = LIQUID
V & L = MIXED

The present invention accomplishes several improvements to the prior art process. Among these improvements are the following: the top section of the low temperture distillation column, the intermediate condenser and the overhead condenser are combined into a single dephlegmator, and the light fuel gas separator is eliminated. Thus, three pieces of equipment in the original process are combined into one and a separator, along with a large amount of interconnecting piping, are eliminated entirely. All of this provides a significant savings in captial. More significantly, the pressure of the carbon dioxide gas stream recovered for reinjection or other use, stream 60, can be substantially increased. In the description of FIG. 2 above, the carbon dioxide gas can be recovered at 250 psia, as compared to 100 psia as is provided in the process according to FIG. 1. Based on feed at 65 psia, an operating pressure of 385 psia with 38% carbon dioxide recycle for 70% propane recovery, and carbon dioxide compression to 2000 psia for reinjection, the present invention provides a 15% reduction in the overall compression energy required for the process.

The present invention has been described with reference to the preferred embodiment thereof. However, this embodiment should not be considered a limitation on the scope of the invention, which scope should be ascertained by the following claims.

We claim:

1. In a process for the separation of a carbonaceous off-gas stream containing a quantity of acid gases, such as carbon dioxide, hydrogen sulfide and carbonyl sulfide, wherein said off-gas stream is compressed, cooled and separated in a low temperature distillation column into a fuel gas stream which is recovered from the top portion of said distillation column, a liquefied acid gas sidestream and a bottoms liquids stream, the improvement comprising (a) incorporating a dephlegmator as the top portion of said distillation column;

(b) passing at least a portion of said liquefied acid gas sidestream to the dephlegmator for indirect heat exchange with distillation column fluids thereby providing refrigeration for said dephlegmator; and (c) subcooling at least a porton of the bottoms liquids stream and passing said subcooled bottoms liquids stream to the dephlegmator for indirect heat exchange with distillation column fluids thereby providing refrigeration for said dephlegmator.

2. The process of claim 1 wherein said off-gas is separated in a two-tier distillation column.

3. The process according to claim 1 wherein said off-gas is derived from a carbon dioxide miscible flood enhanced oil recovery operation.

4. The process according to claim 1 wherein said low temperature distillation column is operated at a pressure in the range of 200 to 650 psia.

5. In a process for the separation of a pressurized carbonaceous off-gas stream containing a quantity of acid gases, such as carbon dioxide, hydrogen sulfide and carbonyl sulfide, wherein said off-gas stream is cooled and separated in a low temperature distillation column into a fuel gas stream which is recovered from the top portion of said distillation column, a liquefied acid gas sidestream and a bottoms liquids stream, the improvement comprising (a) incorporating a dephlegmator as the top portion of said distillation column;

(b) passing at least a portion of said liquefied acid gas sidestream to the dephlegmator for indirect heat exchange with distillation column fluids thereby providing refrigeration for said dephlegmator; and (c) subcooling at least a portion of the bottoms liquids stream and passing said subcooled bottoms liquids stream to the dephlegmator for indirect heat exchange with distillation column fluids thereby providing refrigeration for said dephlegmator.

6. The process of claim 5 wherein said off-gas is separated in a two-tier distillation column.

7. The process according to claim 5 wherein said off-gas is derived from a carbon dioxide miscible flood enhanced oil recovery operation.

8. The process according to claim 5 wherein said low temperature distillation column is operated at a pressure in the range of 200 to 650 psia.

* * * * *